(12) United States Patent
Tokizawa et al.

(10) Patent No.: US 6,737,434 B2
(45) Date of Patent: May 18, 2004

(54) IMIDAZOLE DERIVATIVES OR THEIR SALTS

(75) Inventors: Minoru Tokizawa, Chiba (JP); Sunao Takeda, Chiba (JP); Yasushi Kaneko, Chiba (JP); Koji Kusano, Chiba (JP); Hiromichi Eto, Chiba (JP); Koichi Tachibana, Chiba (JP); Susumu Sato, Chiba (JP); Tadayoshi Taniyama, Kanagawa (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 10/380,828

(22) PCT Filed: Sep. 21, 2001

(86) PCT No.: PCT/JP01/08231

§ 371 (c)(1), (2), (4) Date: Mar. 19, 2003

(87) PCT Pub. No.: WO02/24660

PCT Pub. Date: Mar. 28, 2002

(65) Prior Publication Data

US 2003/0176482 A1 Sep. 18, 2003

(30) Foreign Application Priority Data

Sep. 22, 2000 (JP) .......................................... 2000-288589
Dec. 26, 2000 (JP) .......................................... 2000-394273

(51) Int. Cl.$^7$ ................. C07D 233/60; A61K 31/4164
(52) U.S. Cl. ..................................... 514/399; 548/341.1
(58) Field of Search ........................ 548/341.1; 514/399

(56) References Cited

U.S. PATENT DOCUMENTS

| 4,432,989 A | * 2/1984 | Spencer ...................... 514/399 |
| 4,740,601 A | 4/1988 | Ogawa et al. |
| 4,894,385 A | 1/1990 | Kawamoto et al. |

FOREIGN PATENT DOCUMENTS

| DE | 3907600 A1 * | 9/1990 |
| JP | 61-267557 | 11/1986 |
| JP | 63-146864 | 6/1988 |
| JP | 7-291936 | 11/1995 |
| WO | 97/44033 | 11/1997 |

* cited by examiner

*Primary Examiner*—Laura L. Stockton
(74) *Attorney, Agent, or Firm*—Oblon, Spivak, McClelland, Maier & Neustadt, P.C.

(57) ABSTRACT

Imidazole derivatives of the formula (1) or salts thereof, pharmaceuticals containing the derivatives or the salts, and intermediates for the synthesis of the derivatives or the salts (wherein $R^1$ is lower alkyl; $R^2$ is alkyl or aralkyl; and $X^1$ is halogeno). These compounds exhibit G-CSF-like activities and can be substituted for G-CSF preparations.

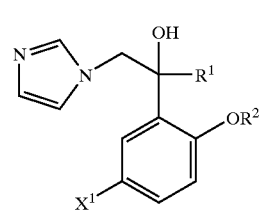

(1)

31 Claims, 2 Drawing Sheets

IMIDAZOLE DERIVATIVES OR THEIR SALTS

CROSS-REFERENCE TO RELATED APPLICATIONS

This application is a national-stage filing under 35 U.S.C. 371 of PCT/JP01/08231, filed Sep. 21, 2001. This application also claims priority to JAPAN 2000-288589, filed Sep. 22, 2000 and JAPAN 2000-394273, filed Dec. 26, 2000.

TECHNICAL FIELD

The present invention relates to novel imidazole derivatives exhibiting cytokine-like activities; in particular, activities analogous to those exhibited by granulocyte-colony stimulating factor (hereinafter referred to as "G-CSF").

BACKGROUND ART

G-CSF drugs have been found effective in therapy of immune diseases which accompany reduction in neutrophils caused by chemotherapy or radiotherapy of cancer. In clinical settings, a human gene recombinant G-CSF injection (Sankyo Co., Ltd.) or similar products are currently employed as G-CSF drugs. However, the G-CSF injection involves drawbacks; namely, it produces problematic side effects, such as inflammation, bone pain, fever, and chill, and upon oral administration it is rapidly degraded, because it is composed of glycoproteins. Therefore, in order to solve these problems, there remains need for development of a low-molecular weight compound which exhibits G-CSF-like activity and which can serve as a substitute for G-CSF drugs. However, presently, very few compounds, such as those described in WO97/44033, are known to exhibit G-CSF-like activities.

Accordingly, an object of the present invention is to provide a novel low-molecular-weight compound exhibiting cytokine-like activities, particularly G-CSF-like activities.

Numerous studies have been carried out on imidazole compounds for possible application as agrochemicals or pharmaceuticals. Of the imidazole compounds, those having a 2-alkoxyphenyl group are reported in Japanese Patent Application Laid-Open (kokai) Nos. 63-146864 or 61-267557. However, these publications fail to mention whether or not those compounds exhibit cytokine-like activities. Moreover, a 2-alkoxyphenyl derivative having a halogen group at the 5-position of the phenyl group has not yet been reported.

DISCLOSURE OF THE INVENTION

Under the above circumstances, the present inventors performed screening tests on a variety of compounds, in search of low-molecular-weight compound having G-CSF-like activities, and have found that a novel class of imidazole derivatives (1) having a 2-alkoxy-5-halogenophenyl group exhibits cytokine-like activities; in particular, G-CSF-like activities, thus leading to completion of the invention.

The present invention provides an imidazole derivative represented by the following formula (1):

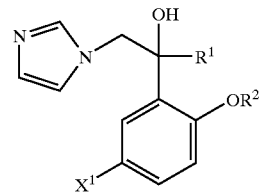

(wherein $R^1$ represents a lower alkyl group, $R^2$ represents an alkyl or aralkyl group, and $X^1$ represents a halogen atom) or a salt thereof, and an intermediate for the synthesis of the derivative or the salt.

The present invention also provides a drug containing an imidazole derivative of formula (1) or a salt thereof as an active ingredient.

The present invention also provides a pharmaceutical composition containing an imidazole derivative of formula (1) or a salt thereof, and a pharmacologically acceptable carrier.

The present invention also provides use of an imidazole derivative of formula (1) or a salt thereof in manufacture of a drug.

The present invention further provides a method of treating an immune disease accompanying reduction in neutrophils, the method comprising administration of an imidazole derivative of formula (1) to a patient in need thereof.

BEST MODE FOR CARRYING OUT THE INVENTION

Figure 1:
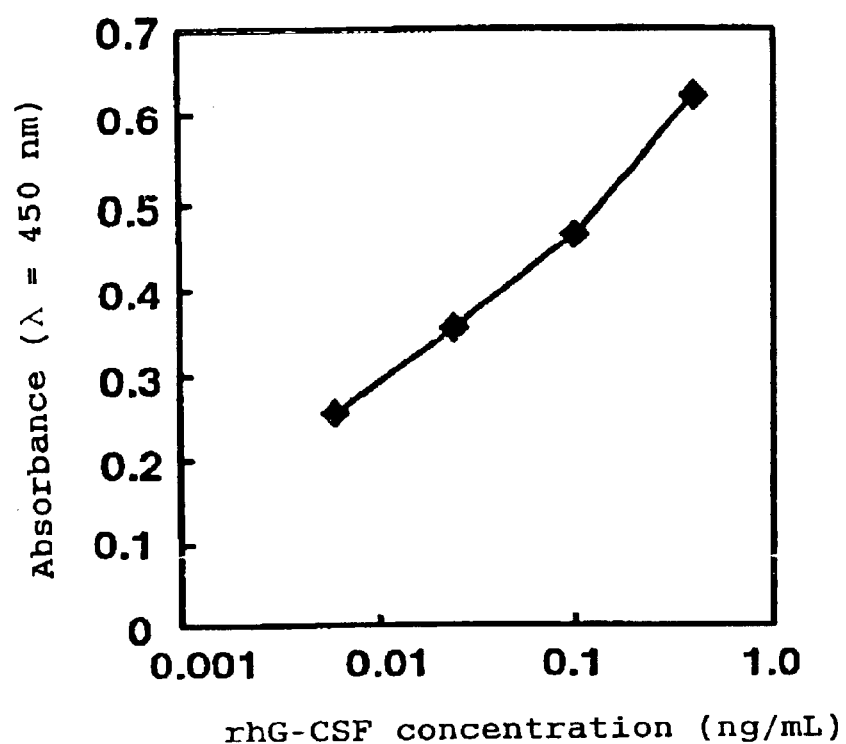
FIG. 1 shows the multiplication ability of human G-CSF-dependent cells in the presence of rhG-CSF.

In formula (1), lower alkyl groups represented by $R^1$ include C1–C5 linear, branched, or cyclic alkyl groups, and specific examples thereof include methyl, ethyl, n-propyl, n-butyl, n-pentyl, and cyclopropyl.

Examples of the alkyl group represented by $R^2$ include C3–C15 linear or branched alkyl groups, and specific examples thereof include n-butyl, n-pentyl, n-hexyl, n-heptyl, n-octyl, n-nonyl, n-decyl, n-undecyl, and n-dodecyl.

Examples of the aralkyl group represented by $R^2$ include phenyl C1–C5 alkyl groups such as benzyl and phenethyl, and halo-substituted groups thereof, and specific examples thereof include benzyl, 4-chlorobenzyl, 2,4-dichlorobenzyl, 2-fluorobenzyl, phenethyl, and 2-fluorophenethyl.

Examples of the halogen represented by $X^1$ include fluorine, chlorine, bromine, and iodine, with fluorine and chlorine being preferred.

No particular limitation is imposed on the salts of the imidazole derivatives (1) of the present invention, so long as they are pharmacologically acceptable salts. Examples of the salts include, but are not limited to, hydrochloride, nitrate, hydrobromide, p-toluenesulfonate, methanesulfonate, fumarate, succinate, and lactate.

The imidazole derivatives (1) or their salts of the present invention have optical isomers based on asymmetric carbon atoms, and optically active compounds and mixtures of isomers such as racemic modifications are encompassed by the present invention. In addition, hydrates of these compounds are also encompassed by the present invention.

The imidazole derivatives (1) or their salts of the present invention may be produced in accordance with the following reaction formula.

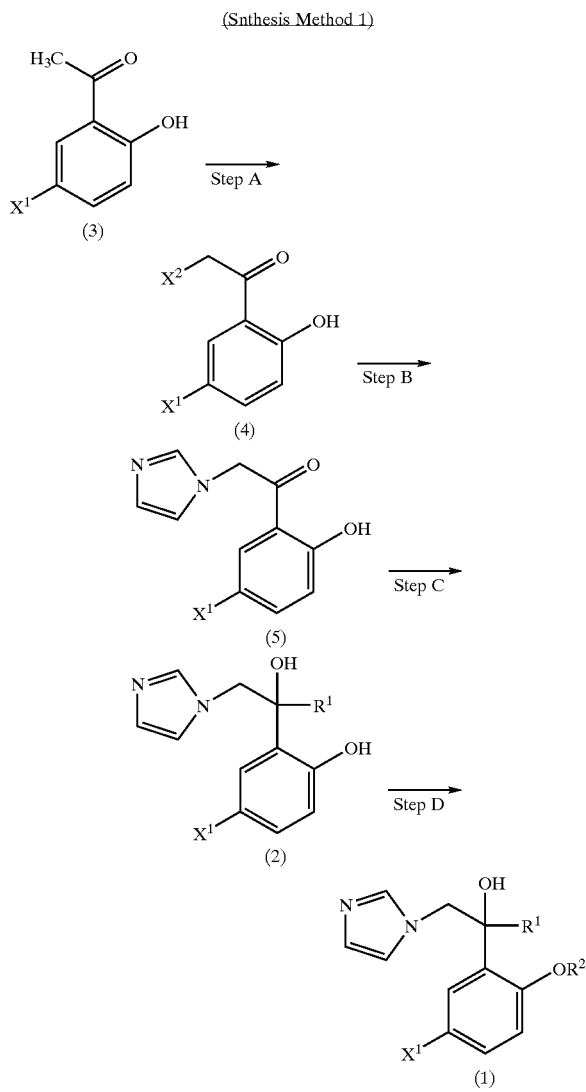

[wherein $R^1$, $R^2$, and $X^1$ have the same meanings as described above, and $X^2$ denotes halogen].

Briefly, a known compound (3) is halogenized, and the resultant haloketone compound (4) is transformed into an imidazole derivative. The obtained compound (5) is subjected to a Grignard reaction, to thereby yield a compound (2), which is finally alkylated or aralkylated, yielding an imidazole derivative (1) of the present invention. In this connection, the compound (2) also is a novel compound, and is useful as an intermediate for the synthesis of imidazole derivative (1). Hereinafter, the synthesis method of the present invention is described in accordance with the above steps.

(Step A)

A halogenizing agent is reacted with compound (3), to thereby yield haloketone compound (4).

Of a variety of compounds (3), examples of preferred class of compounds in which $X^1$ is chlorine or fluorine include those commercially available from Aldorich. Examples of $X^2$ in compound (4) include chlorine, bromine, iodine, with chlorine and bromine being preferred. Preferably, the halogenizing agent is cupric bromide, bromine, sulfuryl chloride, or a similar substance. As the reaction solvent, an ethyl acetate-chloroform solvent mixture, 1,4-dioxane, diethyl ether, a 1,4-dioxane-diethyl ether solvent mixture, acetic acid, dichloromethane, or a similar substance may be used.

(Step B)

Compound (4) is reacted with imidazole, to thereby yield compound (5).

Preferably, the amount of the imidazole to be employed is 2 to 5 equivalents with respect to compound (4). As the reaction solvent, N,N-dimethylformamide, dimethyl sulfoxide, methanol, ethanol, tetrahydrofuran, dioxane, or a similar substance may be used singly or as a mixture, with N,N-dimethylformamide being particularly preferred. Preferably, the reaction temperature is 0 to 50° C., and the reaction time is 1 to 200 hours, more preferably 5 to 48 hours.

(Step C)

Compound (5) is reacted with a Grignard reagent, to thereby attain synthesis of compound (2).

As the Grignard reagent, a compound having the aforementioned lower alkyl group $R^1$ may be used, and examples of the Grignard reagent include methylmagnesium chloride, methylmagnesium bromide, methylmagnesium iodide, ethylmagnesium chloride, ethylmagnesium bromide, propylmagnesium chloride, propylmagnesium bromide, cyclopropylmagnesium chloride, and cyclopropylmagnesium bromide. Preferably, the amount of the Grignard reagent to be employed is 1 to 50 equivalents with respect to compound (5). Preferably, the reaction solvent is tetrahydrofuran, diethyl ether, or a similar substance. Preferably, the reaction temperature is 0 to 50° C., and the reaction time is 1 to 200 hours, more preferably 5 to 48 hours.

(Step D)

Compound (2) is reacted with alkyl halide or aralkyl halide in the presence of a base, to thereby yield compound (1) of the present invention.

As the alkyl halide or aralkyl halide, a halide having the aforementioned $R^2$ as an alkyl group or aralkyl group may be used. Examples of halogens of the halide include chlorine, bromine, and iodine, with bromine being particularly preferred. The amount of the alkyl halide or aralkyl halide to be employed is preferably 1 to 50, more preferably 1 to 10 equivalents with respect to compound (2). Examples of bases include sodium hydroxide, potassium hydroxide, barium hydroxide, sodium carbonate, potassium carbonate, sodium hydride, potassium hydride, sodium methoxide, sodium ethoxide, pyridine, and triethylamine, with sodium hydroxide and potassium hydroxide being particularly preferred. The amount of the base to be employed is preferably 1 to 50, more preferably 1 to 10 equivalents with respect to compound (2). Any reaction solvents may be employed so long as they do not react with the starting compound. For example, there may be employed amides such as N,N-dimethylformamide and N,N-dimethylacetamide; alcohols such as methanol, ethanol, 1-propanol, 2-propanol, 1-butanol, 2-methyl-2-propanol, ethylene glycol, propylene glycol, glycerin, and methyl cellosolve; ethers such as tetrahydrofuran, dioxane, and dimethoxyethane; and dimethyl sulfoxide. These may be used singly or as mixtures. Of these N,N-dimethylformamide is particularly preferred. The reaction temperature is preferably 0 to 100° C., more preferably 10 to 50° C. The reaction time is preferably 1 to 200 hours, more preferably 5 to 48 hours.

The imidazole derivatives (1) or their salts of the present invention can also be produced in accordance with the following reaction formula:

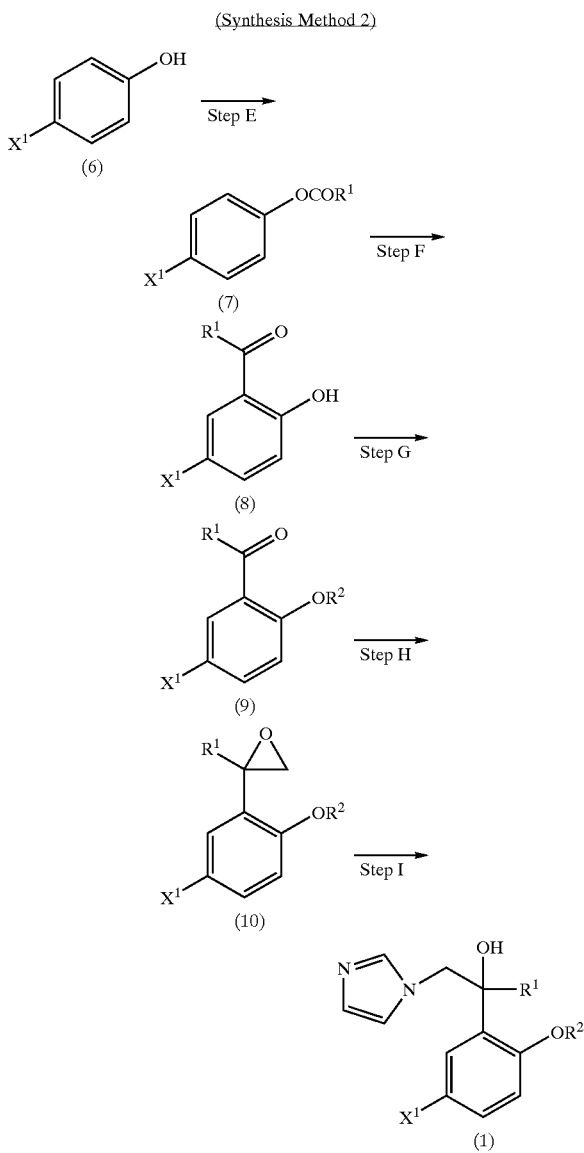

[wherein $R^1$, $R^2$ and $X^1$ have the same meanings as described above].

Briefly, a known compound (6) is acylated, and the resultant compound (7) is subjected to a Fries rearrangement reaction for conversion into compound (8), which is then alkylated or aralkylated to yield compound (9). The compound (9) is epoxidized into a compound (10) and then reacted with an imidazole, to thereby obtain the imidazole derivative (1) of the present invention. The present synthesis method will next be described in accordance with the above steps.

(Step E)

Compound (6) is acylated with acid anhydride, or with acid halide in the presence of a base, to thereby synthesize compound (7).

In the former case, the acid anhydride may be a compound having the aforementioned lower alkyl group $R^1$. Examples of the acid anhydride include acetic anhydride, propionic anhydride, butyric anhydride, and valeric anhydride. The amount of the acid anhydride to be used is preferably 1 to 50, more preferably 1 to 5 equivalents with respect to compound (6). A solvent free system is preferred, but a solvent may be added. Also, a catalytic amount of an acid is desirably added. Examples of the acids include hydrochloric acid, sulfuric acid, and nitric acid, with sulfuric acid being particularly preferred. The reaction temperature is preferably 0 to 100° C., more preferably 10 to 50° C. The reaction time is preferably 1 to 200 hours, more preferably 5 to 48 hours.

In the latter case, the acid halide may be a compound having the aforementioned lower alkyl group $R^1$. For example, mention may be given of acetyl chloride, acetyl bromide, propionyl chloride, propionyl bromide, butyryl chloride, valeryl chloride, and cyclopropanecarbonyl chloride. The amount of the acid halide to be employed is preferably 1 to 50, more preferably 1 to 5 equivalents with respect to compound (6). Preferably, the reaction solvent is dichloromethane or a similar substance. Preferably, the base is pyridine, triethylamine, or a similar substance. The amount of the base to be employed is preferably 1 to 50, more preferably 1 to 5 equivalents with respect to compound (6). The reaction temperature is preferably −20 to 100° C., more preferably 0 to 50° C. The reaction time is preferably 1 to 200 hours, more preferably 5 to 48 hours.

(Step F)

Compound (7) is heated in the presence of a Lewis acid, in the presence or absence of a reaction solvent, to thereby synthesize compound (8).

Examples of the Lewis acid include aluminum chloride, aluminum bromide, zinc chloride, zinc bromide, and stannic chloride, with aluminum chloride being particularly preferred. The amount of the Lewis acid to be employed is preferably 1 to 50, more preferably 1 to 5 equivalents with respect to compound (7). Preferably, the reaction solvent is dichloromethane or a similar substance. Solvent-free systems are also preferred. The reaction temperature is preferably −20 to 200° C., more preferably 20 to 150° C. The reaction time is preferably 10 to 100 hours, more preferably 1 to 20 hours.

(Step G)

Compound (8) is reacted with alkyl halide or aralkyl halide in the presence of a base, to thereby synthesize compound (9).

The alkyl halide or aralkyl halide employable in this step, as well as reaction conditions, are the same as those described in step D of Synthesis Method 1.

(Step H)

Compound (9) is reacted with an epoxidizing agent in a solvent in the presence of a base, or with diazomethane in a solvent, to thereby synthesize compound (10).

In the former case, examples of the epoxidizing agents include trimethylsulfoxonium iodide, trimethylsulfoxonium bromide. Preferably, the amount of the epoxidizing agent to be employed is 1 to 2 equivalents with respect to compound (9). Examples of the bases include sodium hydroxide, potassium hydroxide, barium hydroxide, sodium methoxide, sodium carbonate, potassium carbonate, and sodium hydride, with sodium hydride being particularly preferred. Preferably, the amount of the base to be employed is 1 to 5 equivalents with respect to compound (9). As the solvent, dimethyl sulfoxide, tetrahydrofuran, or a similar substance may be used singly or as a mixture. The reaction temperature is preferably −100° C. to the boiling point of the solvent, more preferably −40 to 50° C. The reaction time is preferably 5 minutes to 100 hours, more preferably 1 to 24 hours.

In the latter case using diazomethane, preferably, diethyl ether or a similar substance is used as solvent. The reaction temperature is preferably −50° C. to the boiling point of the solvent, more preferably −20 to 30° C. The reaction time is preferably 0.5 to 100 hours, more preferably 1 to 24 hours.
(Step I)

Imidazole is reacted with compound (10), to thereby yield compound (1) of the present invention.

Preferably, the amount of the imidazole to be employed is 2 to 5 equivalents with respect to compound (10). As the reaction solvent, N,N-dimethylformamide, dimethyl sulfoxide, methanol, ethanol, tetrahydrofuran, dioxane, or a similar substance may be used singly or as a mixture. In particular, use of N,N-dimethylformamide is preferred. Preferably, the reaction temperature is 20 to 100° C. The reaction time is preferably 1 to 200 hours, more preferably 3 to 48 hours.

In the above-described synthesis methods, no particular limitation is imposed on the means for separating a target compound and the reaction solvent. Examples of the means include, but are not limited to, filtration, extraction, distillation, wash, recrystallization, and chromatography.

The present compound (1) may be transformed into pharmaceutically acceptable salts; including inorganic salts based on inorganic acids such as hydrochloric acid, sulfuric acid, nitric acid, phosphoric acid, and hydrobromic acid; and organic salts based on organic acids such as fumaric acid, maleic acid, acetic acid, malic acid, tartaric acid, citric acid, methanesulfonic acid, and p-toluenesulfonic acid.

The compounds (1) of the present invention or salts thereof exhibit excellent cytokine-like activity, in particular, G-CSF-like activity, and are endowed with high safety and high solubility to aqueous media, thus proving that they are suitably employed for formulation of intravenous injections, and finding utility as a drug for prevention and treatment of immune diseases accompanying reduced neutrophil count in animals and humans.

The present compound (1) or their salts can be formed into various dosage forms such as tablets, granules, powders, capsules, suspensions, injections, and suppositories, through a conventional method. When the compound of the present invention is formed to have a solid form, a vehicle may further be added, and when needed, other additives such as a binder, a disintegrant, a bulking agent, a coating agent, and a sugar coating agent may also be added, and the resultant mixture is processed through a conventional method, to thereby produce solid dosage forms such as tablets, granules, and capsules. In the case where injections are produced, the present compound is dissolved, dispersed, or emulsified in an aqueous carrier (e.g., distilled water for injection); or processed to a powder for preparing an injection, which powder is dissolved upon use. In the case where suppositories are prepared, an oily base or an emulsion base is added to the present compound, and the resultant mixture is processed through a conventional method.

The daily dose of the compound (1) of the present invention or salts thereof for an adult is preferably about 0.05 mg to 5 g, more preferably 1 to 100 mg, which is administered in a single dose or several divided doses.

EXAMPLES

The present invention will next be described in more detail by way of Examples, which should not be construed as limiting the invention.

Referential Example 1

Synthesis of 2-Bromo-1-(5-chloro-2-hydroxyphenyl)-1-ethanone [Compound (4-1)]

A solution of 1-(5-chloro-2-hydroxyphenyl)-1-ethanone [compound (3-1)] (41 g, 0.24 mol) in chloroform (250 mL) was added to a suspension of cupric bromide (107.8 g, 0.48 mol) in ethyl acetate (250 mL), and the resultant mixture was stirred with reflux for 8 hours. After the mixture was cooled on ice, dichloromethane (500 mL) was added, and insoluble matter was filtered off, and the solvent was evaporated. Crystals that precipitated were collected by addition of dichloromethane, washed with dichloromethane, and dried with application of air flow, to thereby yield 2-bromo-1-(5-chloro-2-hydroxyphenyl)-1-ethanone as colorless crystals (35.8 g, yield: 60.0%).

$^1$H-NMR (CDCl$_3$) δ: 4.40 (2H, s), 6.97 (1H, d, J=8 Hz), 7.47 (1H, dd, J=8 Hz, J=2 Hz), 7.73 (1H, d, J=2 Hz), 11.60 (1H, s).

Referential Example 2

Synthesis of 2-Bromo-1-(5-fluoro-2-hydroxyphenyl)-1-ethanone [Compound (4-2)]

The general procedure of Referential Example 1 was repeated, except that 1-(5-fluoro-2-hydroxyphenyl)-1-ethanone [compound (3-2)] was used instead of 1-(5-chloro-2-hydroxyphenyl)-1-ethanone [compound (3-1)], to thereby yield 2-bromo-1-(5-fluoro-2-hydroxyphenyl)-1-ethanone as colorless crystals (yield: 80.4%).

$^1$H-NMR (CDCl$_3$) δ: 4.38 (2H, s), 6.8–7.6 (3H, m), 11.47 (1H, s).

Referential Example 3

Synthesis of 1-(5-Chloro-2-hydroxyphenyl)-2-(1H-1-imidazolyl)-1-ethanone [compound (5-1)]

Imidazole (17.9 g, 0.26 mol) was added to a solution of 2-bromo-1-(5-chloro-2-hydroxyphenyl)-1-ethanone [compound (4-1)] (21.8 g, 87.7 mmol) in N,N-dimethylformamide (50 mL), and the resultant mixture was stirred for 17 hours at room temperature. The reaction mixture was added to ice-water, followed by extraction with ethyl acetate. The organic layer was washed with water, and dried over magnesium sulfate. Subsequently, the solvent was removed under reduced pressure. The residue was purified through silica gel column chromatography, followed by drying under reduced pressure, to thereby yield 1-(5-chloro-2-hydroxyphenyl)-2-(1H-1-imidazolyl)-1-ethanone as colorless crystals (17.1 g, yield: 82.4%).

$^1$H-NMR (DMSO-d$_6$) δ: 5.56 (2H, s), 6.7–7.9 (6H, m), 10.3–10.7 (1H, m).

Referential Example 4

Synthesis of 1-(5-Fluoro-2-hydroxyphenyl)-2-(1H-1-imidazolyl)-1-ethanone [Compound (5-2)]

The general procedure of Referential Example 3 was repeated, except that 2-bromo-1-(5-fluoro-2-hydroxyphenyl)-1-ethanone [compound (4-2)], to thereby yield 1-(5-fluoro-2-hydroxyphenyl)-2-(1H-1-imidazolyl)-1-ethanone as colorless crystals (yield: 86.5%).

$^1$H-NMR (DMSO-d$_6$) δ: 5.81 (2H, s), 6.7–8.0 (7H, m).

Referential Example 5

Synthesis of 4-Chlorophenyl Acetate [Compound (7-1)]

Acetic anhydride (80.1 g, 0.78 mol) and one drop of concentrated sulfuric acid were added to 4-chlorophenol [compound (6-1)] (100 g, 0.78 mol) at room temperature, and the mixture was stirred for 17 hours. The resultant mixture was added to ice-water, and converted to alkaline by the addition of sodium hydroxide (20% aqueous solution), followed by extraction with diethyl ether. The organic layer was washed with water, dried over magnesium sulfate. Subsequently, the solvent was removed under reduced pressure, and then the residue was subjected to distillation under reduced pressure (81° C./1.5 mmHg), to thereby yield 4-chlorophenyl acetate as a colorless oily product (130 g, yield: 98.0%).

$^1$H-NMR (CDCl$_3$) δ: 2.25 (3H, s), 6.97 (2H, d, J=8 Hz), 7.30 (2H, d, J=8 Hz).

Referential Example 6

Synthesis of 1-(5-Chloro-2-hydroxyphenyl)-1-ethanone [Compound (3-1)]

4-chlorophenyl acetate [compound (7-1)] (50 g, 0.293 mol) and aluminum chloride powder (117 g, 0.88 mol) were mixed, and the mixture was stirred for 2 hours at 110° C. The resultant mixture was cooled to room temperature and added to ice-water, followed by extraction with diethyl ether. The organic layer was washed with water, and dried over magnesium sulfate. The solvent was removed under reduced pressure, to thereby yield 1-(5-chloro-2-hydroxyphenyl)-1-ethanone as colorless crystals (40.2 g, yield: 80.4%).

$^1$H-NMR (CDCl$_3$) δ: 2.62 (3H, s), 6.90 (1H, d, J=8 Hz), 7.39 (1H, dd, J=8 Hz, J=2 Hz), 7.65 (1H, d, J=2 Hz), 12.14 (1H, s).

Referential Example 7

Synthesis of 1-(2-(Benzyloxy)-5-chlorophenyl)-1-ethanone [Compound (9-1)]

Potassium carbonate powder (2.9 g, 21.0 mmol) and benzyl bromide (2.3 g, 18.2 mmol) was added to a solution of 1-(5-chloro-2-hydroxyphenyl)-1-ethanone [compound (8-1)] (3.0 g, 17.6 mmol) in dimethylformamide (50 mL), and the mixture was stirred for 3 hours at 60° C. After cooling, ice-water was added to the resultant mixture, followed by extraction with ethyl acetate. The mixture was washed with aqueous sodium hydroxide (5%) and water, and dried over magnesium sulfate. The solvent was removed under reduced pressure, to thereby yield compound (9-1) as a colorless oily product (4.6 g, yield: 99.9%).

$^1$H-NMR (CDCl$_3$) δ: 2.58 (3H, s), 5.14 (2H, s), 6.8–8.8 (3H, m), 7.39 (5H, s).

Referential Example 8

Synthesis of 2-(2-(Benzyloxy)-5-chlorophenyl)-2-methyloxirane [Compound (10-1)]

A suspension of 60% sodium hydride (1.2 g, 30 mmol) in tetrahydrofuran (30 mL)-dimethyl sulfoxide (30 mL) was heated at external temperature of 60° C., and trimethylsulfoxonium iodide (6.5 g, 30 mmol) was added portionwise to the mixture. The resultant mixture was stirred for 1 hour and then cooled to room temperature. A solution of 1-(2-(benzyloxy)-5-chlorophenyl)-1-ethanone [compound (9-1)] (5.0 g, 19 mmol) in tetrahydrofuran (10 mL) was added dropwise to the mixture, and the mixture was stirred for 3 hours at external temperature of 60° C. After the mixture was cooled to room temperature, the mixture was added to ice-water, followed by extraction with diethyl ether. The extracted substance was washed with water and dried over magnesium sulfate. The solvent was removed under reduced pressure, to thereby yield 2-(2-(benzyloxy)-5-chlorophenyl)-2-methyloxirane as a colorless oily product (yield: 4.4 g). The obtained product was used in the subsequent reaction step without purification.

$^1$H-NMR (CDCl$_3$) δ: 1.63 (3H, s), 2.74 (1H, d, J=5.3 Hz), 2.90 (1H, d, J=5.3 Hz), 5.10 (2H, s), 6.6–7.6 (3H, m), 7.38 (5H, s).

Example 1

Synthesis of 4-Chloro-2-(1-hydroxy-2-(1H-1-imidazolyl)-1-methylethyl)phenol [Compound (2-1)]

A suspension of 1-(5-chloro-2-hydroxyphenyl)-2-(1H-1-imidazolyl)-1-ethanone [compound (5-1)] (2.37 g, 10 mmol) in tetrahydrofuran (200 mL) was added to a solution of methylmagnesium bromide in tetrahydrofuran (1 mol/L, 100 mL, 0.1 mol) under cooling with ice, and the mixture was stirred for 17 hours at room temperature. The solvent was removed, a solution of saturated ammonium chloride was added to the resultant mixture, followed by extraction with ethyl acetate. The organic layer was washed with water and dried over magnesium sulfate. The solvent was removed under reduced pressure. Subsequently, the residue was purified through silica gel column chromatography and dried under reduced pressure, to thereby yield 4-chloro-2-(1-hydroxy-2-(1H-1-imidazolyl)-1-methylethyl)phenol as colorless crystals (620 mg, yield: 24.5%).

$^1$H-NMR (CDCl$_3$) δ: 1.63 (3H, s), 4.13 (1H, d, J=14 Hz), 4.32 (1H, d, J=14 Hz), 6.6–7.3 (5H, m), 7.37 (1H, s), 8.90 (2H, br.).

Example 2

Synthesis of 4-Chloro-2-(1-hydroxy-1-(1H-1-imidazolylmethyl)butyl)phenol [Compound (2-2)]

The general procedure of Example 1 was repeated using 1-(5-chloro-2-hydroxyphenyl)-2-(1H-1-imidazolyl)-1-ethanone [compound (5-1)] and n-propylmagnesium bromide, to thereby yield 4-chloro-2-(1-hydroxy-1-(1H-1-imidazolylmethyl)butyl)phenol as a colorless oily product (yield: 50.4%).

$^1$H-NMR (CDCl$_3$) δ: 0.7–1.1 (3H, m), 1.1–2.4 (4H, m), 4.14 (1H, d, J=14 Hz), 4.28 (1H, d, J=14 Hz), 6.5–7.5 (6H, m), 7.7–8.1 (2H, m).

Example 3

Synthesis of 4-Chloro-2-(1-cyclopropyl-1-hydroxy-2-(1H-1-imidazolyl)ethyl)phenol [Compound (2-3)]

The general procedure of Example 1 was repeated using 1-(5-chloro-2-hydroxyphenyl)-2-(1H-1-imidazolyl)-1-ethanone [compound (5-1)] and cyclopropylmagnesium bromide, to thereby yield 4-chloro-2-(1-cyclopropyl-1-hydroxy-2-(1H-1-imidazolyl)ethyl)phenol as colorless crystals (yield: 36.0%).

$^1$H-NMR (CDCl$_3$) δ: 0.2–0.7 (4H, m), 1.0–1.5 (1H, m), 4.30 (1H, d, J=14 Hz), 4.38 (1H, d, J=14 Hz), 6.6–7.5 (6H, m), 7.9–8.3 (2H, br.).

Example 4

Synthesis of 4-Fluoro-2-(1-hydroxy-2-(1H-1-imidazolyl)-1-methylethyl)phenol [Compound (2-4)]

The general procedure of Example 1 was repeated using 1-(5-fluoro-2-hydroxyphenyl)-2-(1H-1-imidazolyl)-1- ethanone [compound (5-2)] and methylmagnesium bromide, to thereby yield 4-fluoro-2-(1-hydroxy-2-(1H-1-imidazolyl)-1-methylethyl)phenol as colorless crystals (yield: 53.2%).

$^1$H-NMR (CDCl$_3$) δ: 1.57 (3H, s), 4.12 (1H, d, J=14 Hz), 4.27 (1H, d, J=14 Hz), 6.6–6.9 (5H, m), 7.35 (1H, s), 8.23 (2H, br.).

Example 5

Synthesis of 4-Fluoro-2-(1-hydroxy-1-(1H-1-imidazolylmethyl)butyl)phenol [Compound (2-5)]

The general procedure of Example 1 was repeated using 1-(5-fluoro-2-hydroxyphenyl)-2-(1H-1-imidazolyl)-1-ethanone [compound (5-2)] and n-propylmagnesium bromide, to thereby yield 4-fluoro-2-(1-hydroxy-1-(1H-1-imidazolylmethyl)butyl)phenol as a colorless oily product (yield: 31.3%).

$^1$H-NMR (CDCl$_3$) δ: 0.7–1.1 (3H, m), 1.1–2.3 (4H, m), 4.18 (1H, d, J=14 Hz), 4.29 (1H, d, J=14 Hz), 6.5–7.5 (6H, m), 8.1–8.8 (2H, m).

Example 6

Synthesis of 2-(5-Chloro-2-(n-nonyloxy)phenyl)-1-(1H-1-imidazolyl)-2-propanol [Compound (1-1)]

Sodium hydroxide powder (20 mg, 0.5 mmol) and n-nonyl bromide (122 mg, 0.59 mmol) were added to a solution of 4-chloro-2-(1-hydroxy-2-(1H-1-imidazolyl)-1-methylethyl)phenol [compound (2-1)] (100 mg, 0.40 mmol) in N,N-dimethylformamide (1 mL), and the mixture was stirred for 17 hours at room temperature. Ice-water was added to the resultant mixture, followed by extraction with ethyl acetate. The organic layer was washed with water and dried over magnesium sulfate. The solvent was removed under reduced pressure. The residue was purified through silica gel column chromatography and dried under reduced pressure, to thereby yield 2-(5-chloro-2-(n-nonyloxy)phenyl)-1-(1H-1-imidazolyl)-2-propanol as a colorless oily product (81.7 mg, yield: 54.5%).

$^1$H-NMR (CDCl$_3$) δ: 0.7–1.0 (3H, m), 1.0–2.2 (14H, m), 1.53 (3H, s), 4.02 (2H, t, J=6 Hz), 4.33 (2H, s), 4.83 (1H, s), 6.6–7.6 (6H, m).

Example 7

Synthesis of 2-(5-Chloro-2-(n-heptyloxy)phenyl)-1-(1H-1-imidazolyl)-2-propanol [Compound (1-2)]

The general procedure of Example 6 was repeated using 4-chloro-2-(1-hydroxy-2-(1H-1-imidazolyl)-1-methylethyl)phenol [compound (2-1)] and n-heptyl bromide, to thereby yield 2-(5-chloro-2-(n-heptyloxy)phenyl)-1-(1H-1-imidazolyl)-2-propanol as a colorless oily product (yield: 74.3%).

$^1$H-NMR (CDCl$_3$) δ: 0.7–1.0 (3H, m), 1.0–2.2 (10H, m), 1.53 (3H, s), 4.02 (2H, t, J=6 Hz), 4.33 (2H, s), 4.83 (1H, s), 6.6–7.6 (6H, m).

Example 8

Synthesis of 2-(5-Chloro-2-(n-octyloxy)phenyl)-1-(1H-1-imidazolyl)-2-propanol [Compound (1-3)]

The general procedure of Example 6 was repeated using 4-chloro-2-(1-hydroxy-2-(1H-1-imidazolyl)-1-methylethyl)phenol [compound (2-1)] and n-octyl bromide, to thereby yield 2-(5-chloro-2-(n-octyloxy)phenyl)-1-(1H-1-imidazolyl)-2-propanol as a colorless oily product (yield: 75.5%).

$^1$H-NMR (CDCl$_3$) δ: 0.7–1.0 (3H, m), 1.0–2.2 (12H, m), 1.53 (3H, s), 4.02 (2H, t, J=6 Hz), 4.31 (2H, s), 4.79 (1H, s), 6.6–7.6 (6H, m).

Example 9

Synthesis of 2-(5-Chloro-2-((2,4-dichlorobenzyl)oxy)phenyl)-1-(1H-1-imidazolyl)-2-propanol [Compound (1-4)]

The general procedure of Example 6 was repeated using 4-chloro-2-(1-hydroxy-2-(1H-1-imidazolyl)-1-methylethyl)phenol [compound (2-1)] and 2,4-dichlorobenzyl chloride, to thereby yield 2-(5-chloro-2-((2,4-dichlorobenzyl)oxy)phenyl)-1-(1H-1-imidazolyl)-2-propanol as colorless crystals (yield: 51.9%).

$^1$H-NMR (CDCl$_3$) δ: 1.49 (3H, s), 4.29 (2H, s), 4.80 (1H, s), 5.16 (2H, s), 6.6–7.7 (9H, m).

Example 10

Synthesis of 2-(5-Chloro-2-(phenethyloxy)phenyl)-1-(1H-1-imidazolyl)-2-propanol [Compound (1-5)]

The general procedure of Example 6 was repeated using 4-chloro-2-(1-hydroxy-2-(1H-1-imidazolyl)-1-methylethyl)phenol [compound (2-1)] and phenethyl chloride, to thereby yield 2-(5-chloro-2-(phenethyloxy)phenyl)-1-(1H-1-imidazolyl)-2-propanol as a colorless oily product (yield: 12.4%).

$^1$H-NMR (CDCl$_3$) δ: 1.38 (3H, s), 3.14 (2H, t, J=6 Hz), 4.06 (2H, s), 4.30 (2H, t, J=6 Hz), 4.43 (1H, s), 6.4–7.4 (6H, m), 7.29 (5H, s).

Example 11

Synthesis of 2-(5-Chloro-2-(n-pentyloxy)phenyl)-1-(1H-1-imidazolyl)-2-pentanol [Compound (1-6)]

The general procedure of Example 6 was repeated using 4-chloro-2-(1-hydroxy-1-(1H-1-imidazolylmethyl)butyl)phenol [compound (2-2)] and n-pentyl bromide, to thereby yield 2-(5-chloro-2-(n-pentyloxy)phenyl)-1-(1H-1-imidazolyl)-2-pentanol as a colorless oily product (yield: 79.9%).

$^1$H-NMR (CDCl$_3$) δ: 0.6–1.1 (6H, m), 1.1–2.5 (10H, m), 4.00 (2H, t, J=6 Hz), 4.22 (1H, d, J=14 Hz), 4.34 (1H, d, J=14 Hz), 4.5–4.7 (1H, br.), 6.5–7.6 (6H, m).

Example 12

Synthesis of 2-(5-Chloro-2-((2,4-dichlorobenzyl)oxy)phenyl)-1-(1H-1-imidazolyl)-2-pentanol [Compound (1-7)]

The general procedure of Example 6 was repeated using 4-chloro-2-(1-hydroxy-1-(1H-1-imidazolylmethyl)butyl)phenol [compound (2-2)] and 2,4-dichlorobenzyl chloride, to thereby yield 2-(5-chloro-2-((2,4-dichlorobenzyl)oxy)phenyl)-1-(1H-1-imidazolyl)-2-pentanol as a colorless oily product (yield: 30.0%).

$^1$H-NMR (CDCl$_3$) δ: 0.6–1.0 (3H, m), 1.0–2.5 (4H, m), 4.20 (1H, d, J=14 Hz), 4.31 (1H, d, J=14 Hz), 4.3–4.6 (1H, br.), 5.11 (2H, s), 6.4–7.6 (9H, m).

Example 13

Synthesis of 2-(5-Chloro-2-((2-fluorophenethyl)oxy)phenyl)-1-(1H-1-imidazolyl)-2-pentanol [Compound (1-8)]

The general procedure of Example 6 was repeated using 4-chloro-2-(1-hydroxy-1-(1H-1-imidazolylmethyl)butyl)

phenol [compound (2-2)] and 2-fluorophenethyl chloride, to thereby yield 2-(5-chloro-2-((2-fluorophenethyl)oxy)phenyl)-1-(1H-1-imidazolyl)-2-pentanol as a colorless oily product (yield: 7.4%).

$^1$H-NMR (CDCl$_3$) δ: 0.6–1.0 (3H, m), 1.0–2.3 (4H, m), 3.20 (2H, t, J=6 Hz), 4.1–4.5 (5H, m), 6.5–7.6 (10H, m).

Example 14

Synthesis of 1-(5-Chloro-2-(n-pentyloxy)phenyl)-1-cyclopropyl-2-(1H-1-imidazolyl)-1-ethanol [Compound (1-9)]

The general procedure of Example 6 was repeated using 4-chloro-2-(1-cyclopropyl-1-hydroxy-2-(1H-1-imidazolyl)ethyl)phenol [compound (2-3)] and n-pentyl bromide, to thereby yield 1-(5-chloro-2-(n-pentyloxy)phenyl)-1-cyclopropyl-2-(1H-1-imidazolyl)-1-ethanol as a colorless oily product (yield: 71.3%).

$^1$H-NMR (CDCl$_3$) δ: 0.1–0.7 (4H, m), 0.7–1.1 (3H, m), 1.1–2.3 (7H, m), 4.02 (2H, t, J 6 Hz), 4.20 (1H, s), 4.36 (1H, d, J=14 Hz), 4.52 (1H, d, J=14 Hz), 6.6–7.5 (6H, m).

Example 15

Synthesis of 1-(5-Chloro-2-(n-octyloxy)phenyl)-1-cyclopropyl-2-(1H-1-imidazolyl)-1-ethanol [Compound (1-10)]

The general procedure of Example 6 was repeated using 4-chloro-2-(1-cyclopropyl-1-hydroxy-2-(1H-1-imidazolyl)ethyl)phenol [compound (2-3)] and n-octyl bromide, to thereby yield 1-(5-chloro-2-(n-octyloxy)phenyl)-1-cyclopropyl-2-(1H-1-imidazolyl)-1-ethanol as a colorless oily product (yield: 58.1%).

$^1$H-NMR (CDCl$_3$) δ: 0.1–0.7 (4H, m), 0.7–1.1 (3H, m), 1.1–2.3 (13H, m), 4.02 (2H, t, J=6 Hz), 4.34 (1H, d, J=14 Hz), 4.52 (1H, d, J=14 Hz), 6.6–7.5 (6H, m).

Example 16

Synthesis of 1-(5-chloro-2-(phenethyloxy)phenyl)-1-cyclopropyl-2-(1H-1-imidazolyl)-1-ethanol [Compound (1-11)]

The general procedure of Example 6 was repeated using 4-chloro-2-(1-cyclopropyl-1-hydroxy-2-(1H-1-imidazolyl)ethyl)phenol [compound (2-3)] and phenethyl chloride, to thereby yield 1-(5-chloro-2-(phenethyloxy)phenyl)-1-cyclopropyl-2-(1H-1-imidazolyl)-1-ethanol as colorless crystals (yield: 26.4%).

$^1$H-NMR (CDCl$_3$) δ: 0.1–0.6 (4H, m), 1.0–1.5 (1H, m), 3.16 (2H, t, J=6 Hz), 4.14 (1H, d, J=14 Hz), 4.30 (2H, t, J=6 Hz), 4.34 (1H, d, J=14 Hz), 4.47 (1H, s), 6.5–7.5 (6H, m), 7.28 (5H, s).

Example 17

Synthesis of 2-(5-Fluoro-2-(n-heptyloxy)phenyl)-1-(1H-1-imidazolyl)-2-propanol [Compound (1-12)]

The general procedure of Example 6 was repeated using 4-fluoro-2-(1-hydroxy-2-(1H-1-imidazolyl)-1-methylethyl)phenol [compound (2-4)] and n-heptyl bromide, to thereby yield 2-(5-fluoro-2-(n-heptyloxy)phenyl)-1-(1H-1-imidazolyl)-2-propanol as colorless crystals (yield: 94.3%).

$^1$H-NMR (CDCl$_3$) δ: 0.7–1.0 (3H, m), 1.0–2.2 (10H, m), 1.53 (3H, s), 4.02 (2H, t, J=6 Hz), 4.33 (2H, s), 5.38(1H, s), 6.6–7.4 (6H, m).

Example 18

Synthesis of 2-(5-Fluoro-2-(n-octyloxy)phenyl)-1-(1H-1-imidazolyl)-2-propanol [Compound (1-13)]

The general procedure of Example 6 was repeated using 4-fluoro-2-(1-hydroxy-2-(1H-1-imidazolyl)-1-methylethyl)phenol [compound (2-4)] and n-octyl bromide, to thereby yield 2-(5-fluoro-2-(n-octyloxy)phenyl)-1-(1H-1-imidazolyl)-2-propanol as a colorless oily product (yield: 86.1%).

$^1$H-NMR (CDCl$_3$) δ: 0.7–1.0 (3H, m), 1.0–2.2 (12H, m), 1.53 (3H, s), 4.00 (2H, t, J=6 Hz), 4.35 (2H, s), 5.47 (1H, s), 6.6–7.4 (6H, m).

Example 19

Synthesis of 2-(5-Fluoro-2-(n-nonyloxy)phenyl)-1-(1H-1-imidazolyl)-2-propanol [Compound (1-14)]

The general procedure of Example 6 was repeated using 4-fluoro-2-(1-hydroxy-2-(1H-1-imidazolyl)-1-methylethyl)phenol [compound (2-4)] and n-nonyl bromide, to thereby yield 2-(5-fluoro-2-(n-nonyloxy)phenyl)-1-(1H-1-imidazolyl)-2-propanol as a colorless oily product (yield: 88.4%).

$^1$H-NMR (CDCl$_3$) δ: 0.7–1.0 (3H, m), 1.0–2.2 (14H, m), 1.53 (3H, s), 4.00 (2H, t, J=6 Hz), 4.33 (2H, s), 4.84 (1H, s), 6.6–7.4 (6H, m).

Example 20

Synthesis of 2-(2-((2,4-Dichlorobenzyl)oxy)-5-fluorophenyl)-1-(1H-1-imidazolyl)-2-propanol [Compound (1-15)]

The general procedure of Example 6 was repeated using 4-fluoro-2-(1-hydroxy-2-(1H-1-imidazolyl)-1-methylethyl)phenol [compound (2-4)] and 2,4-dichlorobenzyl chloride, to thereby yield 2-(2-((2,4-dichlorobenzyl)oxy)-5-fluorophenyl)-1-(1H-1-imidazolyl)-2-propanol as colorless crystals (yield: 31.6%).

$^1$H-NMR (CDCl$_3$) δ: 1.50 (3H, s), 4.24 (1H, s), 4.32 (2H, s), 5.19 (2H, s), 6.6–7.6 (9H, m).

Example 21

Synthesis of 2-(5-Fluoro-2-(phenethyloxy)phenyl)-1-(1H-1-imidazolyl)-2-propanol [Compound (1-16)]

The general procedure of Example 6 was repeated using 4-fluoro-2-(1-hydroxy-2-(1H-1-imidazolyl)-1-methylethyl)phenol [compound (2-4)] and phenethyl chloride, to thereby yield 2-(5-fluoro-2-(phenyloxy)phenyl)-1-(1H-1-imidazolyl)-2-propanol as a colorless oily product (yield: 13.4%).

$^1$H-NMR (CDCl$_3$) δ: 1.41 (3H, s), 3.17 (2H, t, J=6 Hz), 4.07 (2H, s), 4.30 (2H, t, J=6 Hz), 4.57 (1H, s), 6.5–7.5 (6H, m), 7.29 (5H, s).

Example 22

Synthesis of 2-(5-Fluoro-2-(n-pentyloxy)phenyl)-1-(1H-1-imidazolyl)-2-pentanol [Compound (1-17)]

The general procedure of Example 6 was repeated using 4-fluoro-2-(1-hydroxy-1-(1H-1-imidazolylmethyl)butyl)phenol [compound (2-5)] and n-pentyl bromide, to thereby yield 2-(5-fluoro-2-(n-pentyloxy)phenyl)-1-(1H-1-imidazolyl)-2-pentanol as a colorless oily product (yield: 80.3%).

¹H-NMR (CDCl₃) δ: 0.6–1.0 (3H, m), 0.94 (3H, t, J=6 Hz), 1.0–2.5 (10H, m), 3.99 (2H, t, J=6 Hz), 4.14 (1H, s), 4.29 (1H, d, J=14 Hz), 4.42 (1H, d, J=14 Hz), 6.5–7.5 (6H, m).

Example 23

Synthesis of 2-(2-((4-Chlorobenzyl)oxy)-5-fluorophenyl)-1-(1H-1-imidazolyl)-2-pentanol [Compound (1-18)]

The general procedure of Example 6 was repeated using 4-fluoro-2-(1-hydroxy-1-(1H-1-imidazolylmethyl)butyl) phenol [compound (2-5)] and 4-chlorobenzyl chloride, to thereby yield 2-(2-((4-chlorobenzyl)oxy)-5-fluorophenyl)-1-(1H-1-imidazolyl)-2-pentanol as a colorless oily product (yield: 8.1%).

¹H-NMR (CDCl₃) δ: 0.6–1.0 (3H, m), 1.0–2.5 (4H, m), 3.2–3.5 (1H, m), 4.25 (1H, d, J=14 Hz), 4.34 (1H, d, J=14 Hz), 5.02 (2H, s), 6.6–7.6 (10H, m).

Example 24

Synthesis of 2-(2-((2,4-Dichlorobenzyl)oxy)-5-fluorophenyl)-1-(1H-1-imidazolyl)-2-pentanol [Compound (1-19)]

The general procedure of Example 6 was repeated using 4-fluoro-2-(1-hydroxy-1-(1H-1-imidazolylmethyl)butyl) phenol [compound (2-5)] and 2,4-dichlorobenzyl chloride, to thereby yield 2-(2-((2,4-dichlorobenzyl)oxy)-5-fluorophenyl)-1-(1H-1-imidazolyl)-2-pentanol as a colorless oily product (yield: 13.0%).

¹H-NMR (CDCl₃) δ: 0.6–1.0 (3H, m), 1.0–2.5 (4H, m), 3.2–3.6 (1H, m), 4.25 (1H, d, J=14 Hz), 4.36 (1H, d, J=14 Hz), 5.15 (2H, s), 6.5–7.6 (9H, m).

Example 25

Synthesis of 2-(5-Fluoro-2-((2-fluorophenethyl)oxy) phenyl)-1-(1H-1-imidazolyl)-2-pentanol [Compound (1-20)]

The procedure of Example 6 was repeated using 4-fluoro-2-(1-hydroxy-1-(1H-1-imidazolylmethyl)butyl)phenol [compound (2-5)] and 2,4-dichlorobenzyl chloride, to thereby yield 2-(5-fluoro-2-((2-fluorophenethyl)oxy) phenyl)-1-(1H-1-imidazolyl)-2-pentanol as a colorless oily product (yield: 8.0%).

¹H-NMR (CDCl₃) δ: 0.6–1.0 (3H, m), 1.0–2.3 (4H, m), 3.20 (2H, t, J=6 Hz), 3.8–4.5 (5H, m), 6.5–7.5 (10H, m).

Example 26

Synthesis of 2-(2-(Benzyloxy)-5-chlorophenyl)-1-(1H-1-imidazolyl)-2-propanol [Compound (1-21)]

Imidazole (4.0 g, 58.8 mmol) and potassium t-butoxide (6.5 g, 57.9 mmol) were added to a solution of 2-(2-(benzyloxy)-5-chlorophenyl)-2-methyloxirane [compound (10-1), obtained in Referential Example 8] (4.4 g) in dimethylformamide (60 mL), and the mixture was stirred for 12 hours at 80° C. After the mixture was cooled to room temperature, ice-water was added thereto, followed by extraction with ethyl acetate. The organic layer was washed with water and dried over magnesium sulfate. The solvent was removed under reduced pressure. The residue was purified through silica gel column chromatography and dried under reduced pressure, to thereby yield 2-(2-(benzyloxy)-5-chlorophenyl)-1-(1H-1-imidazolyl)-2-propanol as colorless crystals (5.0 g, yield: 75.8%).

¹H-NMR (CDCl₃) δ: 1.47 (3H, s), 4.27 (2H, s), 5.09 (2H, s), 6.5–7.6 (6H, m), 7.42 (5H, s). MS (FAB): 345, 343 (M+H).

Test Example 1

Creation of a Human G-CSF-dependent Cell Strain (in vitro)

Cloning of human G-CSF receptor gene was performed through RT-PCR by using primers created on the basis of the human G-CSF receptor gene using a human spleen cDNA library. The thus cloned human G-CSF receptor gene inserted to a multicloning site of an expression vector. Subsequently, the gene-inserted expression vector was transformed into E. coli for multiplication, and the expression vector was extracted. An aliquot of the expression vector (20 μg) was added to host cells (BAF/B03) prepared to 5×10⁷ cells/800 μL K-PBS (30.8 mM NaCl, 120.7 mM KCl, 8.1 mM Na₂HPO₄, 1.46 mM KH₂PO₄, 5 mM MgCl₂), followed by standing still at 4° C. for 15 minutes. For gene transfer, electroporation was performed at a voltage of 280 V and a capacitance of 950 μF. After completion of gene transfer, the cells were suspended in a DMEM medium ((+) 10% FCS) containing recombinant human G-CSF (rhG-CSF, 20 ng/mL) and puromycin (2 μg/mL), whereby a human G-CSF dependent cell strain was created.

For studying the cell multiplication ability with respect to rhG-CSF, the following procedure was carried out. Briefly, cells in which the human G-CSF receptor gene had been inserted (BAF/hGCSFR) were collected, and washed with PBS(-). Subsequently, the cells were suspended in DMEM medium, and the medium containing the cells was prepared to the wells of a 96-well plate (5×10⁴ cells/well). Then, rhG-CSF was added to the wells (0, 0.006, 0.025, 0.1, 0.4 ng/mL), and the cells in the wells were cultured under 5% CO₂ for 48 hours at 37° C. After completion of incubation, a solution of WST-1/1-methoxy PMS was added to the wells (final concentration: 5 mM), and the cells in the wells were cultured in a CO₂ incubator for 2 hours. After completion of incubation, the absorbance of the cultured solution was measured at a wavelength of 450 nm. The results are shown in FIG. 1 (mean±standard error, n=5).

Test Example 2

Retrieval of Compounds Inducing Cell Growth of a Human G-CSF Dependent Cell Strain (in vitro)

Figure 2:
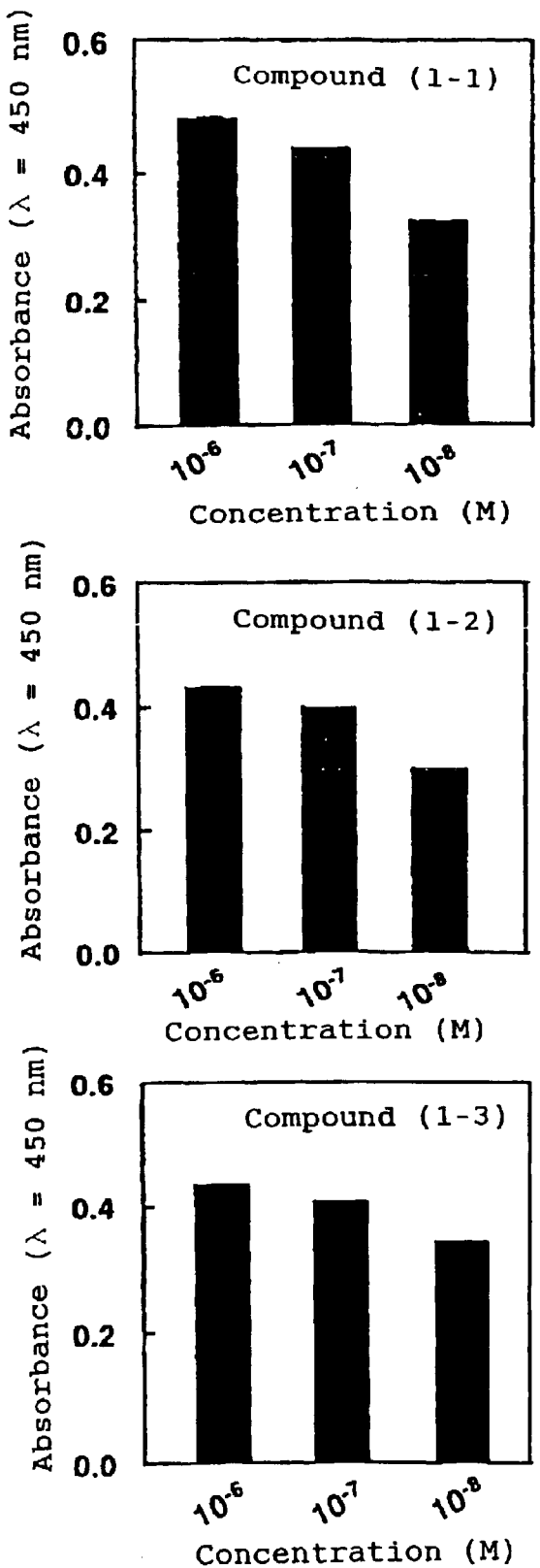
FIG. 2 shows induction of multiplication of human G-CSF-dependent cells by the compound of the present invention.

A solution prepared by diluting a compound with DMEM was added to the wells of a 96-well microplate (10 μL/well). The human G-CSF-dependent cell strain was added to the wells (5.0×10⁴ cells/100 μL), followed by incubation for 48 hours at 37° C. After completion of incubation, a solution of WST-1/1-methoxy PMS (final concentration: 5 mM) was added to the wells, followed by incubation in a CO₂ incubator for 2 hours. After completion of incubation, the absorbance was measured at a wavelength of 450 nm. The results are shown in FIG. 2 (mean±standard error, n=5).

Test Example 3

Human-G-CSF Equivalent Concentrations Corresponding to Respective Compound Concentrations Using the test data obtained from Test Example 1, human-G-CSF equivalent concentrations (ng/mL) corresponding to respective compound concentrations employed in Test Example 2 were calculated. The results are shown in Table 1 (mean±standard error, n=5).

TABLE 1

| compound | compound conc. | | |
|---|---|---|---|
| | $10^{-6}$ M | $10^{-7}$ M | $10^{-8}$ M |
| (1-1) | 0.131 ± 0.001 | 0.032 ± 0.0003 | 0.015 ± 0.0001 |
| (1-2) | 0.049 ± 0.0004 | 0.037 ± 0.0003 | 0.013 ± 0.0001 |
| (1-3) | 0.057 ± 0.0005 | 0.057 ± 0.0005 | 0.018 ± 0.0001 |

Industrial Applicability

The compounds (1) or salts thereof according to the present invention exhibit excellent cytokine-like activity, in particular, G-CSF-like activity, and are endowed with high safety and high solubility to aqueous media, thus proving that they are suitably employed for formulation of intravenous injections, and finding utility as a drug for prevention and treatment of immune diseases accompanying reduced neutrophil count in animals and humans.

What is claimed is:

1. An imidazole derivative represented by the following formula (1):

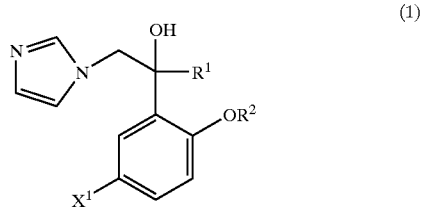

(1)

wherein
$R^1$ represents a lower alkyl group,
$R^2$ represents an at least a $C_6$ alkyl group, or an aralkyl group which may optionally be halo-substituted, and
X represents a halogen atom,
or a salt or a hydrate thereof.

2. An imidazole derivative represented by the following formula (2):

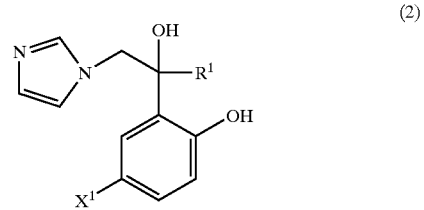

(2)

wherein
$R^1$ represents a lower alkyl group, and
$X^1$ represents a halogen atom,
or a salt thereof.

3. The imidazole derivative of claim 1, wherein $R^1$ is linear alkyl group.

4. The imidazole derivative of claim 1, wherein $R^1$ is branched alkyl group.

5. The imidazole derivative of claim 1, wherein $R^1$ is cyclic alkyl group.

6. The imidazole derivative of claim 1, wherein $R^2$ is n-hexyl, n-heptyl or n-octyl.

7. The imidazole derivative of claim 1, wherein $R^2$ is n-nonyl or n-decyl.

8. The imidazole derivative of claim 1, wherein $R^2$ is n-undecyl or n-dodecyl.

9. The imidazole derivative of claim 1, wherein $R^2$ is a linear alkyl group.

10. The imidazole derivative of claim 1, wherein $R^2$ is a branched alkyl group.

11. The imidazole derivative of claim 1, wherein $R^2$ is phenyl $C_1$–$C_5$ alkyl.

12. The imidazole derivative of claim 1, wherein $R^2$ is a halogen-substituted aralkyl group.

13. The imidazole derivative of claim 1, wherein $X^1$ is a fluorine atom.

14. The imidazole derivative of claim 1, wherein $X^1$ is a chlorine atom.

15. A salt of the imidazole derivative of claim 1 selected from the group consisting of the hydrochloride, nitrate, hydrobromide, p-toluenesulfonate, methanesulfonate, fumate, succinate and lactate.

16. An isomer or mixture of isomers of the derivative of claim 1.

17. A composition comprising the derivative of claim 1 or a salt thereof, and a pharmaceutically acceptable carrier.

18. The composition of claim 17 in a solid dosage form.

19. The composition of claim 17 in a dissolved, dispersed or emulsified form.

20. The composition of claim 17 in an injectable form.

21. The composition of claim 17 in the form of a tablet, capsule or granule.

22. A method for manufacturing a drug or a therapeutic composition comprising:
   admixing the imidazole derivative of claim 1 or a salt or a hydrate thereof with a pharmaceutically acceptable carrier or excipient.

23. A method for inducing G-CSF-like activity, comprising administering to a subject in need thereof the imidazole derivative of claim 1.

24. The method of claim 23 comprising administering a dose ranging from 0.05 mg to 5 g of said imidazole derivative.

25. A method for treating an immune disease accompanying a pathological condition with a reduction in neutrophils, comprising:
   administering to a subject in need thereof the imidazole derivative of claim 1 or a salt thereof.

26. A method for making the imidazole derivative of claim 1 comprising:
   reacting an imidazole derivative of formula (2) with an alkyl halide or aralkyl halide in the presence of a base, wherein formula (2) is:

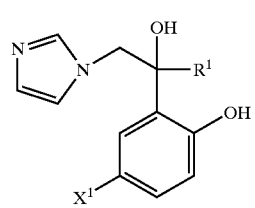

(2)

wherein
$R^1$ represents a lower alkyl group, and
$X^1$ represents a halogen atom,
or a salt thereof.

27. The imidazole derivative of claim 2, wherein $R^1$ is a linear alkyl group.

28. The imidazole derivative of claim 2, wherein $R^1$ is a branched alkyl group.

29. The imidazole derivative of claim 2, wherein $R^1$ is cyclic alkyl group.

30. The imidazole derivative of claim 2, wherein $X^1$ is a fluorine atom.

31. The imidazole derivative of claim 2, wherein $X^1$ is a chlorine atom.

* * * * *

UNITED STATES PATENT AND TRADEMARK OFFICE
CERTIFICATE OF CORRECTION

PATENT NO. : 6,737,434 B2
DATED : May 18, 2004
INVENTOR(S) : Minoru Tokizawa et al.

It is certified that error appears in the above-identified patent and that said Letters Patent is hereby corrected as shown below:

Column 17,
Line 39, "represents an at least a" should read -- represents at least a --;
Line 41, "X represents a" should read -- $X^1$ represents a --.

Signed and Sealed this

Ninth Day of November, 2004

JON W. DUDAS
*Director of the United States Patent and Trademark Office*